United States Patent [19]
Megerle et al.

[11] Patent Number: 5,965,882
[45] Date of Patent: *Oct. 12, 1999

[54] MINIATURIZED ION MOBILITY SPECTROMETER SENSOR CELL

[75] Inventors: Clifford A. Megerle, Thousand Oaks; Carl W. Townsend, Los Angeles; Jacques F. Linder, Palos Verdes, all of Calif.

[73] Assignee: Raytheon Company, Lexington, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/946,115

[22] Filed: Oct. 7, 1997

[51] Int. Cl.$^6$ ........................................................ H01J 49/40
[52] U.S. Cl. .............................................................. 250/287
[58] Field of Search ............................................. 250/287

[56] References Cited

U.S. PATENT DOCUMENTS

| | | | |
|---|---|---|---|
| 4,390,784 | 6/1983 | Browning et al. | 250/287 |
| 5,455,417 | 10/1995 | Sacristan | 250/287 |

Primary Examiner—Jack I. Berman
Attorney, Agent, or Firm—Colin M. Raufer; Leonard A. Alkov; Glenn H. Lenzen, Jr.

[57] ABSTRACT

An improved ion mobility spectrometer for detecting chemical warfare agents and hazardous vapors. The ion mobility spectrometer has an improved sensor cell that includes a heated air flow assembly, an ionization assembly and a field electrode and detector assembly printed circuit assembly. The heated air flow assembly includes a cover with an air inlet, an ambient temperature sensor, a thin-film heater element, a heater frame, a heated air sensor, and a heater channel formed therein. The ionization assembly comprises a nuclear ionization source attached to a holder, a lid, and an ionization channel formed therein that is coupled to the heater channel. The field electrode and detector assembly printed circuit assembly comprises a field electrode printed circuit board, a detector electrode printed circuit board, and detector electronics. The field electrode printed circuit board has a plurality of field electrodes disposed on a bottom surface thereof. A gasket is disposed between the field electrode and detector electrode printed circuit boards. The detector electrode printed circuit board has a plurality of detector electrodes disposed on a top surface thereof. The detector electronics processes current outputs of the detector electrodes to generate a histogram of ion currents that identify mobilities of chemical species tested by the ion mobility spectrometer.

18 Claims, 3 Drawing Sheets

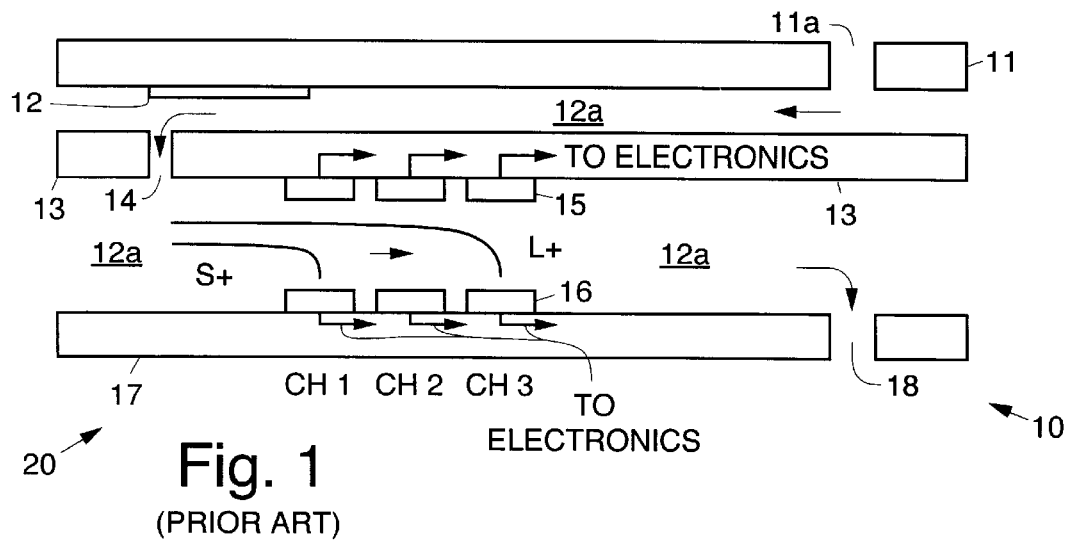
Fig. 1
(PRIOR ART)
Fig. 1a
(PRIOR ART)
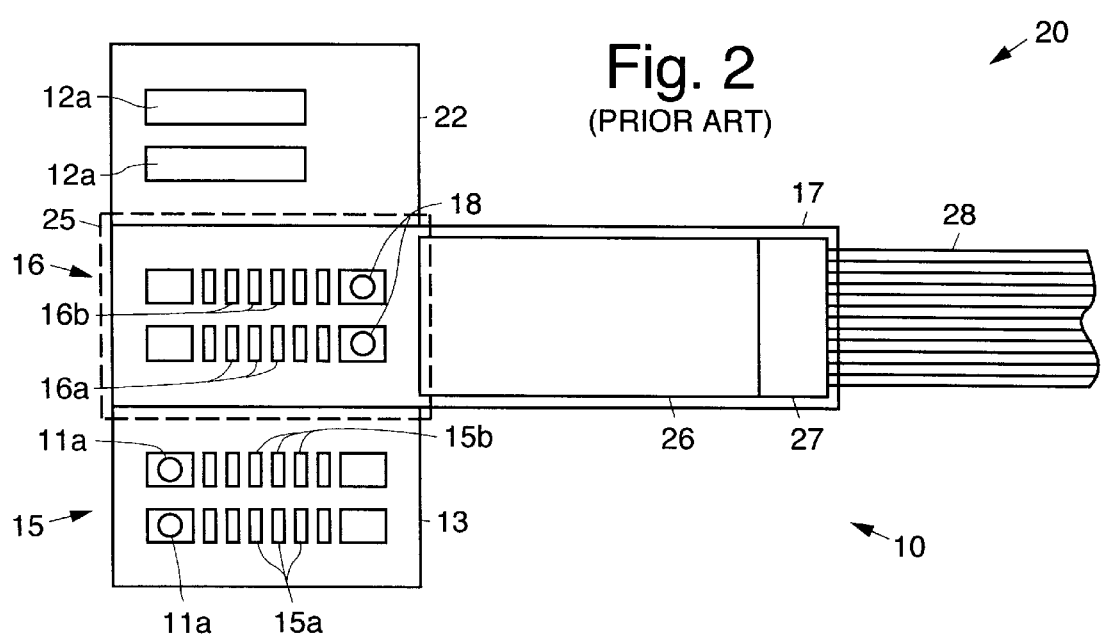
Fig. 2
(PRIOR ART)

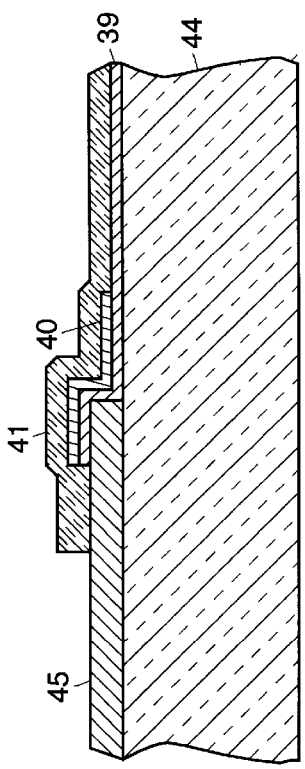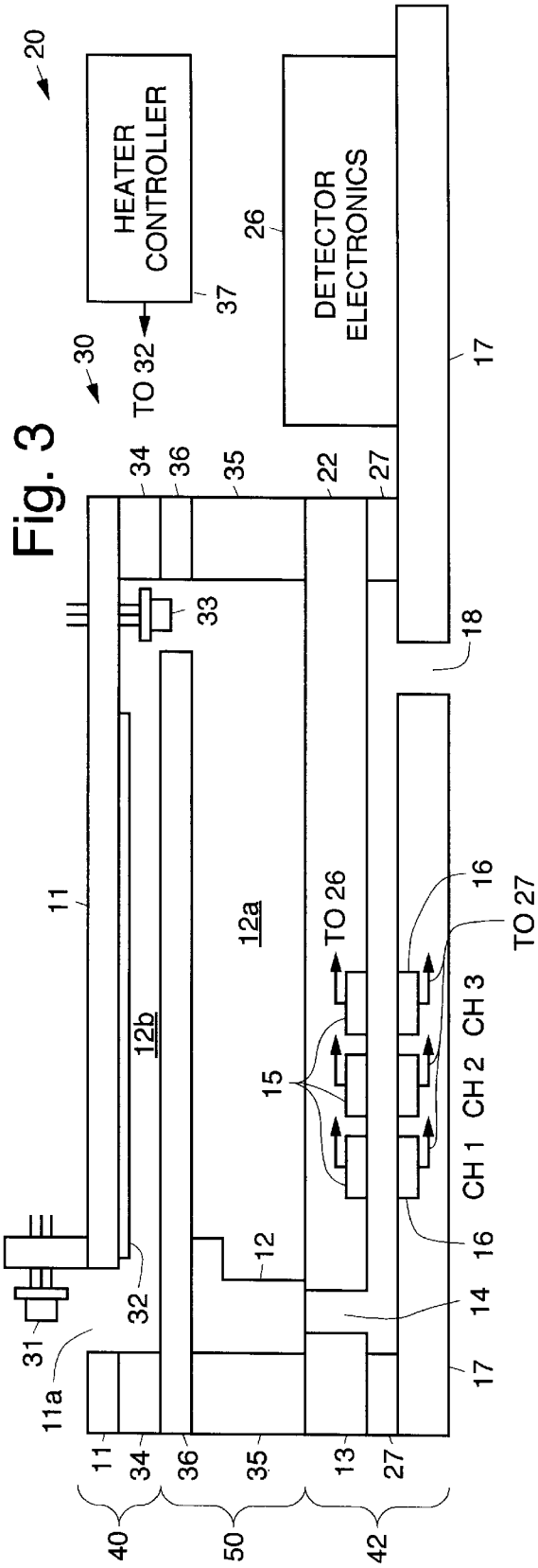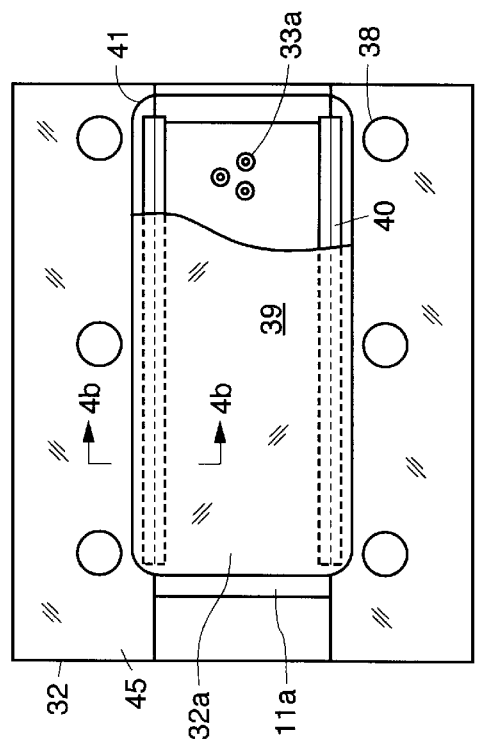

5,965,882

MINIATURIZED ION MOBILITY SPECTROMETER SENSOR CELL

BACKGROUND

The present invention relates generally to ion mobility spectrometers and sensors, and more particularly, to a miniaturized ion mobility sensor and spectrometer that may be used as a chemical sensor.

All known commercially available ion mobility spectrometers and sensors use isotopic ionization sources. One such ion mobility spectrometer is disclosed in U.S. Pat. No. 5,047,723 entitled "Method for Detection of Foreign Matter Contents in Gases", issued Sep. 10, 1991, for example. The assignee of this patent, Environics, Oy of Finland manufactures ion mobility spectrometers for use in detecting chemicals.

This patent discloses the use of an ionized carrier gas containing foreign matter that is passed through chambers with different electric fields. The foreign matter is ionized by the ions in the air, the ions are collected at electrodes in the chambers, and the ion currents passing through one or more chambers are measured, and corresponding signals are obtained. The amounts and relationships of these signals permit analysis of the foreign matter contained in the gasses. The ionization source disclosed in this patent is an isotopic ionization source wherein radioactive radiation derived from an Americium ionization source ionizes the carrier gas and the molecules of the foreign matter contained in it.

However, the ion mobility spectrometer manufactured by Environics, Oy, for example, is quite large. It would be advantageous to have an ion mobility spectrometer that is smaller in size than the large-sized spectrometers available from Environics, Oy, for example. It would also be advantageous to have an ion mobility spectrometer that performs as well as or better than other commercially available small-sized spectrometers, such as those made by Graseby, for example.

Accordingly, it is an objective of the present invention to provide for a miniaturized ion mobility spectrometer that may be used as a chemical sensor.

SUMMARY OF THE INVENTION

To accomplish the above and other objectives, the present invention provides for an improved ion mobility spectrometer for chemical warfare agents, and in particular to a spectrometer developed by Environics, Oy of Finland. The present ion mobility spectrometer comprises an improved sensor cell that includes an air flow heater assembly, an ionization assembly and a field electrode and detector assembly printed circuit assembly.

The heated air flow assembly comprises a cover having an air inlet, an ambient temperature sensor, a thin-film heater element, a heater frame, a heated air sensor, and a heater channel formed therein. The ionization assembly comprises a nuclear ionization source attached to a holder, a lid, and an ionization channel formed therein that is coupled to the heater channel.

The field electrode and detector assembly printed circuit assembly comprises a field electrode printed circuit board, a detector electrode printed circuit board, and detector electronics. The field electrode printed circuit board has a plurality of field electrodes disposed on a bottom surface thereof. A gasket is disposed between the field electrode and detector electrode printed circuit boards. The detector electrode printed circuit board has plurality of detector electrodes disposed on a top surface thereof. The detector electronics processes current outputs of the detector electrodes to generate histogram of ion currents that identify mobilities of chemical species tested by the ion mobility spectrometer.

One of the objectives of the present invention is to reduce the size of the existing detector cell manufactured by Environics, Oy from its present size of 11"×4"×11" to a size of approximately 40 in$^3$ or less. To accomplish this goal, the Environics, Oy sensor cell, which has a size of approximately 6"×4"×2" has been miniaturized using the principles of the present invention to occupy a small amount of its normal space. At the same time, the performance of the sensor has not been compromised.

The present invention reduces the size of the sensor cell to 5½"×1¾"×¾", a volume of 7.2 in$^3$, without changing the critical dimensions of the portion of the sensor cell that performs the analytical chemistry function. Substantial further size reductions are possible with only minor changes to the detector electronics.

The present invention thus miniaturizes the heart of the chemical warfare agent monitor without altering the design, critical dimensions, or functioning of the ion mobility spectrometer portion of the sensor cell. The advantage is that it makes possible a pocket-sized monitor for chemical warfare agents and other hazardous organic chemical in air. While demand for a pocket-sized sensors is large, there is only a small demand for currently available, large-sized sensor.

The present invention has been developed for use by organizations in detecting chemical warfare agents, as well as commercial organizations for detecting chemicals contained in hazardous waste, and the like.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which:

FIG. 1 is a cutaway side view of a conventional ion mobility spectrometer;

FIG. 1a illustrates the output of the ion mobility spectrometer of FIG. 1;

FIG. 2 is an exploded top view of the ion mobility spectrometer of FIG. 1;

FIG. 3 illustrates an ion mobility spectrometer in accordance with the principles of the present invention;

FIGS. 4a and 4b are top and partial cutaway side views, respectively, of a heating element used in the ion mobility spectrometer of FIG. 3.

DETAILED DESCRIPTION

Figure 5A:
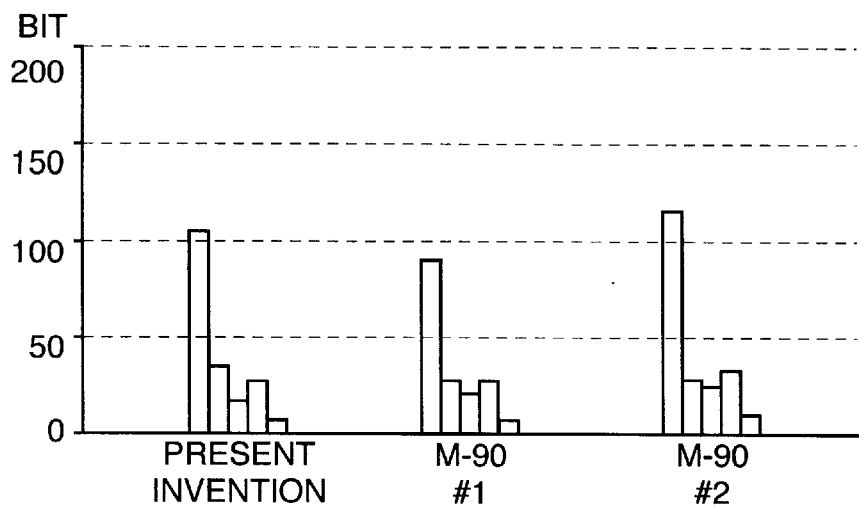
FIGS. 5a–5c show test data generated using the present invention.

Referring to the drawing figures, FIG. 1 illustrates a cutaway side view of a sensor cell 10 of a conventional ion mobility spectrometer 20, such as one manufactured by Environics, Oy and disclosed in U.S. Pat. No. 5,047,723. The ion mobility spectrometer 20 is a simple analytical mechanism that separates ionizable chemical species (or chemical warfare agents) based primarily on their cross-sectional areas and secondarily on their mass. The species in air are ionized by a nuclear ionization source 12 such as Americium-241, and pass into the sensor cell 10 of the spectrometer 20. In the Environics, Oy implementation of the ion mobility spectrometer 20 shown in FIG. 1 and described in U.S. Pat. No. 5,047,723, air enters an air inlet 11a and flows through an ionization channel 12a formed by a cover 11 and an upper printed wiring board 13, through an opening 14 in the upper printed wiring board 13. Ions created by the ionization source 12 are subjected to electric fields that are perpendicular to the direction of air flow created using a plurality of field electrodes 15 formed on the upper printed wiring board 13 and a corresponding plurality of ion collection (detector) electrodes 16 formed on a lower printed wiring board 17.

The ions drift downward (in FIG. 1) in the ionization channel 12a and strike one of the plurality of ion collection electrodes 16, which serves to support the transverse electric field in the cell 10 and collect the ion currents. The rate at which the ions drift downward is determined by their mobilities, which are primarily a function of their charge and cross-sectional areas, and to a lesser extent by their masses. At the same time, they drift to the right (in FIG. 1) because they are carried along with the air stream that passes through the cell 10. Those ions that have a high mobility (small ions, and to a lesser extent, light-weight ions) move rapidly downward, and strike the collection electrodes 16 to the left in FIG. 1. Such ions are labeled "S+".

Those ions that have a low mobility (large ions and, to a lesser extent, heavy ions) move slowly downward, and are carried farther by the stream before they strike an ion collection electrode 16. Therefore, they strike electrodes 16 to the right in FIG. 1. Such ions are labeled "L+" in the figure. A histogram of ion currents, shown in FIG. 1a is used to identify the mobilities of the chemical species (chemical warfare agents) that are ionized and detected in the sensor cell 10. The identities of the chemical species (chemical warfare agents) are known from their mobilities. The ionized air eventually exits the sensor cell 10 through an air outlet 18.

Ionic size and mass also depend, in part, on the temperature and humidity of the incoming air sample. By heating the incoming air to a controlled temperature, uncontrolled effects of temperature and humidity are reduced, and more reproducible histograms are produced. Thus, in normal operation, an air heater is required (not shown).

FIG. 2 illustrates a top view of an Environics, Oy model M-90 ion mobility spectrometer 20 generally described with reference to FIG. 1. The sensor cell 10 of the ion mobility spectrometer 20 is constructed on a lower printed wiring board 17. The bottom half of the ionization channel 12a is formed on the lower printed wiring board 17, and comprises positive and negative ion collection electrodes 16a, 16b (that respectively collect positive and negative ions). The top half of the ionization channel 12a is formed on the upper printed wiring board 13, and comprises the field electrodes 15 that serve to produce the electric field in which the ions of the chemical species (chemical warfare agents) drift. The field electrodes 15 include positive and negative field electrodes 15a, 15b that respectively oppose the positive and negative ion collection electrodes 16a, 16b). A Teflon spacer sheet 22 has cutouts that define the ionization channel 12a (actually two channels 12a) and form their side walls. The air enters the cell 10 through holes comprising the air inlet 11a, passes to the right (in the drawing figure) through the ionization channels 12a defined by the upper and lower printed wiring boards 13, 17 and the Teflon spacer 22, and exits the cell 10 through exit holes comprising the air outlet 18. The field and ion collection electrodes 15a, 15b, 16a, 16b are connected to detector electronics 26 formed on the lower printed wiring board 17. A connector 27 and flat ribbon cable 28 are used to connect the sensor cell 10 to the detector electronics 26, which includes amplifiers, an analog-to-digital converter, a multiplexer device, a digital signal processing circuit, memory devices, and communications and annunciation devices, among other circuits.

In order to heat the incoming air stream, the M-90 ion mobility spectrometer 20 has a large Teflon block 25 (shown with dashed lines) that holds a heater cartridge (not shown). The large Teflon block 25, which has dimensions of 3" tall by 1½" wide by 2" deep, sits on top of the sensor cell 10 of the ion mobility spectrometer 20. The present invention replaces this large Teflon block 25 with a small thin-film surface heater element 32 as will be described with reference to FIGS. 3 and 4.

Referring to FIG. 3, it is a cross sectional view of a sensor cell 30 in accordance with the principles of the present invention for use in an ion mobility spectrometer 20. The present sensor cell 30 comprises a cover 11 having an air inlet 11a therein and an ambient temperature thermistor 31 or other ambient temperature sensor 31 attached to the exterior thereof. The thin-film surface heater element 32, such as may be provided by a tantalum heater element 32, for example, is attached to an interior surface of the cover 11. A heater frame 34 is attached to the cover 11 and forms a thin heater channel 12b through the upper portion of the sensor cell 30. A heated air thermistor 33 or other heated air temperature sensor 33 is disposed in the heater channel 12b downstream of the thin-film surface heater element 32.

A nuclear ionization source 12 is attached to a holder 35. The nuclear ionization source 12 comprises a piece of Americium foil 12 that is attached to the holder 35. An upper lid 36 is attached to the holder 35 and forms inner walls of the ionization channel 12a. An upper, or field electrode printed circuit board 13 abuts the holder 35. The field electrode printed circuit board 13 has an opening 14 therein adjacent to the piece of Americium foil 12 that permits heated air to pass by the piece of Americium foil 12. The space between the upper lid 36, the heater frame 34 and the upper surface of the field electrode printed circuit board 13 forms the ionization channel 12a through which heated air passes. The field electrode printed circuit board 13 also has a plurality of field electrodes 15 disposed on a bottom surface thereof.

A Teflon gasket 27 is disposed between the field electrode printed circuit board 13 and a detector electrode printed circuit board 17 that completes the ionization channel 12a and ends at an air outlet 18. The detector electrode printed circuit board 17 has a plurality of detector electrodes 16 disposed on a top surface thereof. The detector electrode printed circuit board 17 has the air outlet 18 formed therein that permits the ionized air passing through the sensor cell 30 to pass to a humidity sensor and gas sensor (not shown). The detector electrode printed circuit board 17 also has detector electronics 26 disposed thereon that processes current outputs of the detector electrodes 16.

In operation, and with reference to FIG. 3, air to be sampled enters the air inlet 11a and to the ionization channel 12a. Ambient temperature is measured with the ambient temperature thermistor 31 which is disposed in the incoming air flow stream. The air flows past the thin-film surface heater element 32 through the thin heater channel 12b. The air then passes the heated air thermistor 33, which measures the heated air temperature. A feedback control loop which may be part of the detector electronics 26 adjusts the power supplied to the heater element 32 from a heater controller 37 to maintain a constant exit temperature, regardless of the inlet air temperature. This feedback control is performed in a conventional manner. The heated air then passes through the ionization channel 12a which contains the piece of Americium foil 12, which ionizes the air stream. If chemical species (chemical warfare agents or other hazardous vapors) are present in the heated air stream, they pick up charge from the air. Electric fields formed between the field electrodes 15 and the detector electrodes 16 then divert ionized chemical species to the detector electrodes 16, where they are measured and identified based on their mobilities as described above.

The thin-film surface heater element 32 used in the sensor cell 30 of the ion mobility spectrometer 10 is shown in FIGS. 4a and 4b. FIG. 4b is a cross-sectional view of a portion of the heater element 32 taken in the direction of arrows 4b in FIG. 4a. The thin-film surface heater element 32 is made using a combination of printed wiring board techniques and thin-film sputtering. Copper clad circuit board laminate is cut to size and drilled with bolt holes 38 and the air inlet 11a. The copper cladding is stripped from a central region 32a of the heater element 32. A plurality of holes 33a are formed through the central region 32a of the heater element 32 to permit locating the heated air thermistor 33. A thin film of conductive material 39 is sputtered onto the surface of a substrate 44. The resistivity, thickness, width and length of the conductive material 39 is adjusted to match the power requirements of the heater element 32. Simple trial and error techniques using various film thicknesses of the conductive material 39 may be used until the resistance of the heater element 32 is within desired tolerances. To improve the reliability of the electrical contact between a copper contact 45 and the resistive film (conductive material 39), a thin strip of silver-gold alloy 40 is sputtered over the interface. The thin film heater element 32 may be made out of any metal. However, to assure stable operation, the metal should be oxidation resistant. The metal film may be left uncovered, or may be covered with a material 41 which does not strongly adsorb the chemical warfare agent species being tested.

An ion mobility spectrometer 10 and sensor cell 30 as shown in FIG. 3 employing the heater element 32 shown in FIGS. 4a and 4b was constructed and tested. More specifically, FIGS. 4a and 4b are top and side views, respectively, of a heating element 32 used in the ion mobility spectrometer 20 of FIG. 3. Pieces of polyimide printed wiring board laminate were used to form components of the heater channel 12b and the holder 35 for the Americium-241 foil 12. A thin-film tantalum heater element 32 was constructed that was approximately 4,000 Angstroms thick and had a resistance of about 18 ohms. All of the internal components, except for the surface of the heater element 32 were coated with parylene to minimize surface adsorption. The surface of the heater element 32 was coated with a 1 mil thick layer of Kaptone® polyimide, which also minimized surface adsorption. When connected to a 5 volt power supply in the heater controller 37, about 1.4 watts of heat was produced by the heater element 32. A time-proportioning temperature control circuit (not shown) held the temperature to 35° C. during chemical warfare agent testing, and also allows heating to 80° C. during a thermal bake-out cycle for decontamination purposes.

As illustrated in FIG. 3, a heated air flow assembly 40 comprising the heater element 32, thermistors 31, 33, heater frame 34 and cover 11 was attached to an ionization assembly 50 comprising the holder 35 with attached nuclear ionization source 12 and upper lid 36, which were mated to a field electrode and detector assembly printed circuit assembly 42 used in the M-90 spectrometer 20 made by Environics, Oy. Copper laminate edges of the heater element 32 and leads (not shown) to the thermistors 31, 33 were connected to a power supply and heater controller 37. The resulting ion mobility spectrometer sensor cell 30 was installed into a housing of the M-90 spectrometer 20. The overall height of the spectrometer 20 shown in FIG. 4 was ¾", width was 2.2" and the length (which includes preamplifier electronics) was 5½". The size of the heated air flow assembly 40 was 9/32" high, 1.75" wide and 2.2" long, for a volume of 1.08 in$^3$. For comparison purposes, the heated airflow assembly used in the conventional M-90 spectrometer 20 has dimensions of 3" high by 1½" wide by 2" long, for a volume of 9 in$^3$. Because of the space reduction resulting from use of the present heated air flow assembly 40, considerable empty space remained in the original housing. Although not modified for the purposes of the present invention, a simple repackaging effort would substantially reduce the size of the overall spectrometer 20.

The modified ion mobility spectrometer 20 was tested using an air sample containing trace quantities of Dimethoxymethylphosphonate (DMMP), a chemical compound used to simulate chemical warfare agents such as the nerve gas Sarin without the hazards of working with extremely toxic substances. Previous studies have found the ionization and mobility of this compound to be representative of the high toxicity compounds. The spectrometer 20 made in accordance with the present invention produced an ion mobility histogram of the sample and correctly identified the sample as DMMP. Appropriate warning lights and audible alarm were also activated, showing that a nerve agent stimulant had been identified.

Figure 5B:
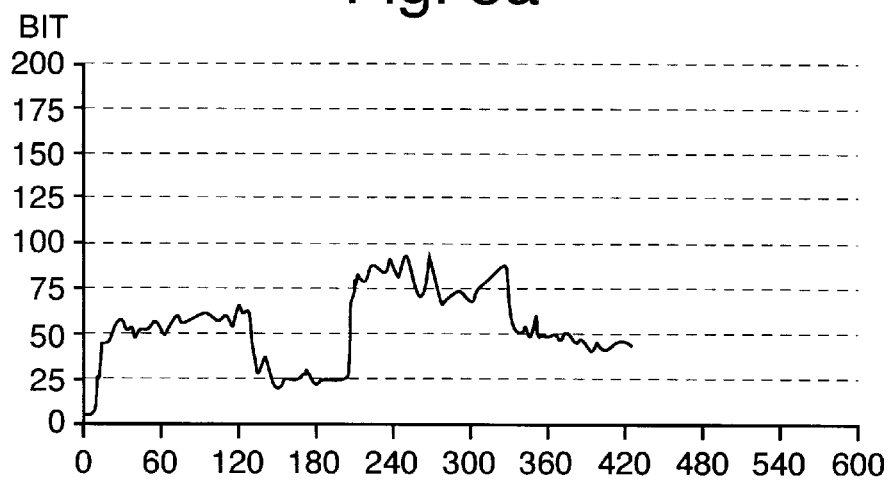
Figure 5C:
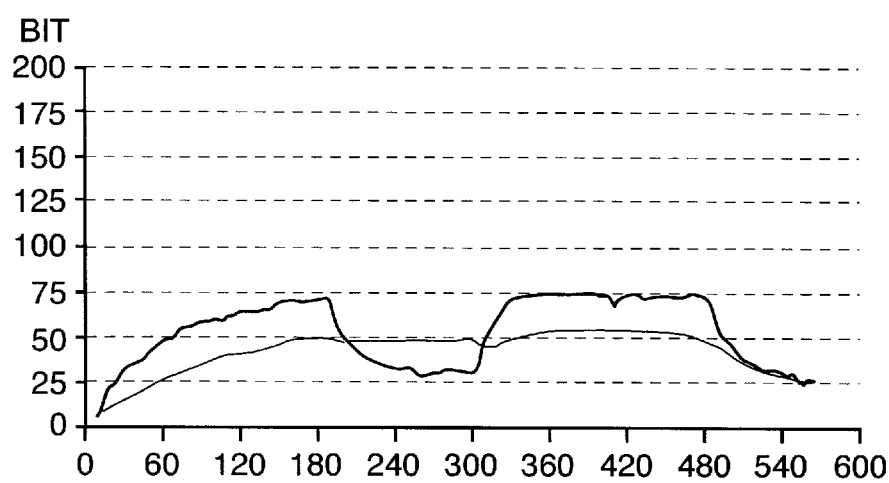

Based on the successful results with simulants, the miniaturized ion mobility spectrometer was tested with two live chemical agents, Soman (GD) and Methylphosphonothioic acid S-[2-[bis(1-methylethyl)amino]ethyl] O-ethyl ester (VX). Results are shown in FIGS. 5a–5c. FIG. 5a shows a histogram of electrode currents of six channels in the sensor cell when exposed to GD. The histogram for the present invention is shown in FIG. 5b and is the same as two versions of the Environics, Oy model M-90 shown in FIG. 5c, showing equal specificity.

FIGS. 5b and 5c compare the detector electrode current as a function of time for one of the six electrodes for the two devices. The response time of the present invention (FIG. 5b) is slightly faster than the baseline M-90 device (FIG. 5c). This results from the smaller channel volume in the present invention, thus allowing the sample to reach the detector electrodes more quickly. Additionally, the parylene coating does not adsorb chemical warfare agents as strongly as the Teflon walls of the heater block 25 in the M-90 device, which otherwise delays travel of the chemical warfare agent through the heater channel. The faster response time of the present invention would allow a soldier more time to don protective gear once an alarm in the field signals the presence of chemical warfare agents.

Thus, a miniaturized ion mobility sensor and spectrometer that may be used as a chemical sensor has been disclosed. It is to be understood that the described embodiment is merely illustrative of some of the many specific embodiments that represent applications of the principles of the present invention. Clearly, numerous and other arrangements can be readily devised by those skilled in the art without departing from the scope of the invention.

What is claimed is:

1. A sensor cell for use in an ion mobility spectrometer, said sensor cell comprising:

a heated air flow assembly comprising an ambient temperature sensor and a thin heater channel and having a thin-film heater element disposed on an interior surface of the channel;

an ionization assembly; and a field electrode and detector assembly printed circuit assembly.

2. The sensor cell of claim 1 wherein the heated air flow assembly further comprises:

a cover having an air inlet;

a heater frame for holding the thin-film heater element;

a heated air sensor; and a heater channel.

3. The sensor cell of claim 2 wherein the ionization assembly comprises:

a nuclear ionization source attached to a holder;

a lid separating the nuclear ionization source from the heated air flow assembly; and an ionization channel coupled to the heater channel.

4. The sensor cell of claim 1 wherein the field electrode and detector assembly printed circuit assembly comprises:

a field electrode printed circuit board comprising a plurality of field electrodes;

a detector electrode printed circuit board comprising a plurality of detector electrodes disposed adjacent to and separated from the plurality of field electrodes;

a gasket disposed between the field electrode and detector electrode printed circuit boards; and detector electronics coupled to the plurality of detector electrodes for processing current outputs thereof to generate a histogram of ion currents.

5. The sensor cell of claim 2 wherein the thin-film surface heater element comprises a tantalum heater element.

6. The sensor cell of claim 3 wherein the nuclear ionization source comprises Americium-241 foil.

7. The sensor cell of claim 3 wherein the gasket comprises a Teflon gasket.

8. The sensor cell of claim 2 wherein the temperature sensors comprise thermistors.

9. A sensor cell for use in an ion mobility spectrometer, said sensor cell comprising:

a cover having an air inlet therein;

an ambient temperature sensor attached to the cover;

a thin-film heater element attached to an interior surface of the cover;

a heater frame attached to the cover that forms a thin heater channel through the upper portion of the sensor cell;

a heated air sensor disposed in the heater channel downstream of the thin-film surface heater element;

a nuclear ionization source attached to a holder;

a lid attached to the holder that forms walls of the heater channel and an ionization channel;

a field electrode printed circuit board disposed adjacent to the holder having an opening therein that permits heated air to pass by the nuclear ionization source and has a plurality of field electrodes disposed on a bottom surface thereof;

a detector electrode printed circuit board having plurality of detector electrodes disposed on a top surface thereof, an air outlet formed therein, and detector electronics disposed thereon, that processes current outputs of the detector electrodes to generate a histogram of ion currents that identify mobilities of chemical species tested by the ion mobility spectrometer; and a gasket disposed between the field electrode printed circuit board and the detector electrode printed circuit board that forms outer walls of the ionization channel.

10. The sensor cell of claim 9 wherein the thin-film surface heater element comprises a tantalum heater element.

11. The sensor cell of claim 9 wherein the nuclear ionization source comprises Americium-241 foil.

12. The sensor cell of claim 9 wherein the gasket comprises a Teflon gasket.

13. The sensor cell of claim 9 wherein the temperature sensors comprise thermistors.

14. An ion mobility spectrometer comprising:

a sensor cell comprising:

a cover having an air inlet therein;

an ambient temperature sensor attached to the cover;

a thin-film heater element attached to an interior surface of the cover;

a heater frame attached to the cover that forms a thin heater channel through the upper portion of the sensor cell;

a heated air sensor disposed in the heater channel downstream of the thin-film surface heater element;

a nuclear ionization source attached to a holder;

a lid attached to the holder that forms walls of the heater channel and an ionization channel;

a field electrode printed circuit board disposed adjacent to the holder having an opening therein that permits heated air to pass by the nuclear ionization source and has a plurality of field electrodes disposed on a bottom surface thereof;

a detector electrode printed circuit board having plurality of detector electrodes disposed on a top surface thereof, an air outlet formed therein, and detector electronics disposed thereon, that processes current outputs of the detector electrodes to generate histogram of ion currents that identify mobilities of chemical species tested by the ion mobility spectrometer; and a gasket disposed between the field electrode printed circuit board and the detector electrode printed circuit board that forms outer walls of the ionization channel.

15. The spectrometer of claim 14 wherein the thin-film surface heater element comprises a tantalum heater element.

16. The spectrometer of claim 14 wherein the nuclear ionization source comprises Americium-241 foil.

17. The spectrometer of claim 14 wherein the gasket comprises a Teflon gasket.

18. The spectrometer of claim 14 wherein the temperature sensors comprise thermistors.

* * * * *